Figure 1:
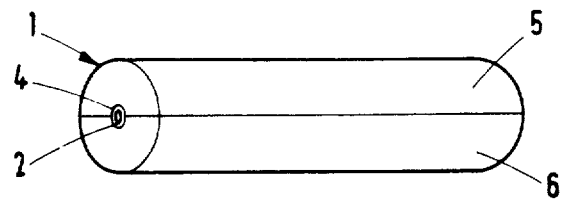

United States Patent [19]

Shepperd

[11] Patent Number: 4,863,476

[45] Date of Patent: Sep. 5, 1989

[54] SPINAL IMPLANT

[76] Inventor: John A. N. Shepperd, Hemingfold, Telham, Near Battle, East Sussex, England

[21] Appl. No.: 90,610

[22] Filed: Aug. 28, 1987

[30] Foreign Application Priority Data

Aug. 29, 1986 [GB] United Kingdom ............... 8620937

[51] Int. Cl.⁴ .............................................. A61F 2/44
[52] U.S. Cl. ..................................................... 623/17
[58] Field of Search ..................... 623/16–23; 128/92 YY, 92 YM, 85

[56] References Cited

U.S. PATENT DOCUMENTS 4,657,550 4/1987 Daher .................................. 623/12

FOREIGN PATENT DOCUMENTS 2324867 11/1974 Fed. Rep. of Germany .... 623/16 F
3119130 3/1983 Fed. Rep. of Germany ........ 623/22

*Primary Examiner*—Richard J. Apley
*Assistant Examiner*—David J. Isabella
*Attorney, Agent, or Firm*—Ladas & Parry

[57] ABSTRACT

A spinal implant has an elongate body which is divided into two portions with mutually opposed contact surfaces and is for insertion into the joint space between two adjacent vertebrae. A cam device or cam devices are movable between the contact surfaces to expand or increase the spacing between the body portions so as to increase the spacing between the adjacent vertebrae.

The implant has a porous external surface to facilitate bore and cartilage tissue growth therein. Alternatively, the external surface is smooth and coated with a bioactive material such as a hydroxyapatite, for example, tricalcium phospahte. In both instances bone, cartilage tissue and external surfaces of the implant are fused together to prevent migration of the implant. Advantageously, insertion of the implant requires a minimum incision in skin and cartilage tissue.

3 Claims, 3 Drawing Sheets

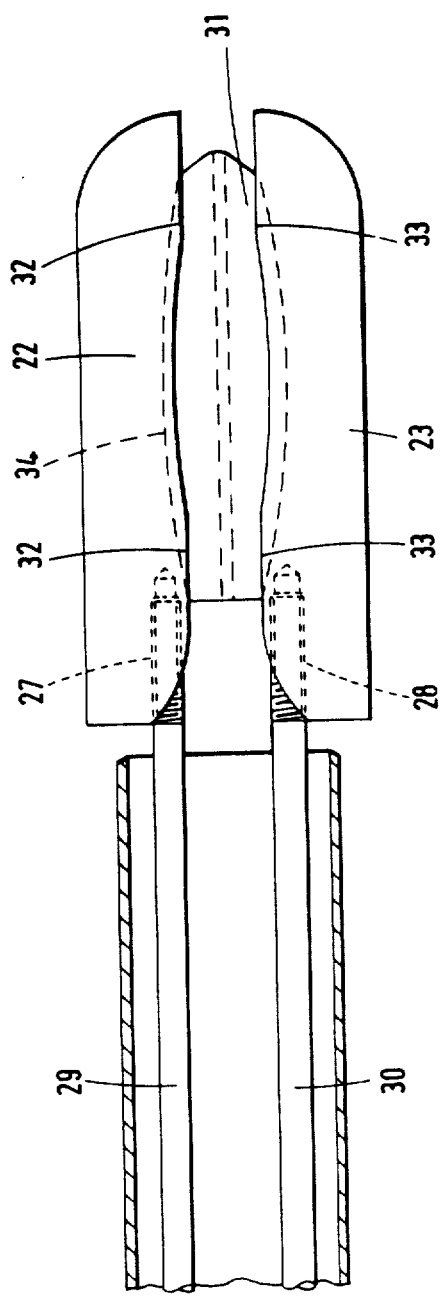
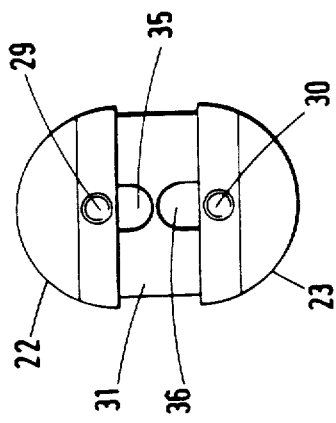

SPINAL IMPLANT

This invention relates to spinal implants.

The spine is a flexible structure of about two feet in length comprising thirty-three vertebrae, twenty-eight of which are separate bones and five of which are fused to form the sacrum. A typical vertebrae consists of bony mass in front, that is the side of the spine closest to the skin, called the body and an arch behind which together form a ring through which the spinal cord passes. Three processes extend from this ring, one at either side called the tansverse processes, and one at the back which is known as the spinous process. These give attachment to the muscles which support and move the vertical column.

The vertebrae move on each other by means of their articular processes, whilst the bodies are separated from each other by thick circular pads of fibro-cartilage, called the inter-vertebral discs, which give the whole structure subtleness and deaden jars. Strong ligaments bind the vertebrae together.

Whereby, by disease or injury, the spine has an unnatural curve, referred to as a scoliosis, it is possible to achieve spinal fusion with the spine in its correct position by using spinal implants. Spinal fusion has been employed for stabilising segments of the spine for a number of decades and various surgical approaoches to the problem are known, including anteria approach and interbody fusion, posterial interspinous fusion, postero-lateral fusion and inter-transverse fusion. In all cases either autograft, homografted or heterograft bone is employed and for some methods an implant is used to achieve immediate fixation.

Interbody fusion with distraction, that is stretching of the spine into a natural position, has been a desirable goal because in distracting vertical end plates, nerve root canal size is increased and thus the risk of nerve root pressure and nerve root irritation is eliminated or reduced. Unfortunately, distracting the vertebral end plates can only be retained by bone graft which in most instances collapses.

One particular type of spinal implant comprises an elongate rod having an attachment device mounted on each of its two ends, the attachment device serving for connection with the spinal column. The rod is rotatable relative to both attachment devices and one of the devices is screw-threadingly attached to the rod so that upon rotation of the rod the attachment device moves longitudinally there to achieve stretching of the spinal column. The rod may have mounted upon it a backing sleeve which is movable along the rod until centered over a superior facet of a fractured or most posteriorly displaced vertebrae. With the sleeves in place moderate distraction can be applied in stages. With correct positioning and selection of sleeve size the injured segments are held in a clinically rigid condition anatomically aligned in all planes. The disadvantage with such arrangements is that they are permanently rigid and have contact with the bone over a relatively small area.

It is desirable therefore to provide a permanent implant to substitute a full bone graft in establishing distraction into body fusion.

According to the present invention there is provided a spinal implant comprising an elongate body divided longitudinally into two portions and being insertable in the joint space between two adjacent vertebrae, engageable contact surfaces between the body portions, and expansion means movable between the contact surfaces of the body portions for spacing body portions apart and adjusting the joint spacing between adjacent vertebrae.

The spinal implant is preferably cylindrical and divided longitudinally into two halves. The body may be divided into more than two portions, preferably four portions. The expansion means is located between the two body portions and preferably comprises an elongate rod having an outer screw thread on at least part of its outer surface and cam means mounted on the screw threaded part. The cam means is of a greater diameter than the internal diameter of the body and sits within an enlarged cavity defined between the body portions.

When the rod is rotated the cam means moves along the rod and forces the two body portions apart as the cam means engages the side walls of the enlarged cavity within the body. The more the rod is turned the further the cam means moves thus increasing the spacing between the body portions.

Preferably the cam means comprises two sleeves each locatable within its own enlarged cavity within the body and being screw-threadedly mounted on the rod. Rotation of the rod in one direction moves the cam means outwardly towards the ends of the body, whilst rotation in the opposite direction moves the cam means towards each other until the cam means meet centrally of the body. In this latter case the body will rock at its extreme ends thus ensuring subtleness between injured or diseased vertebrae.

In a further embodiment of the present invention the implant body has abutting flat contact surfaces which are each provided with a single concave recess which receives the convex surfaces of a cam device which is pushed between the housing or body portions. The body portions each have a threaded bore for receiving the threaded ends of support rods or wires therein and the cam device has elongate grooves therein for freely supporting the wires whilst the cam device is presented to the body portions in the non-distracted condition of the body portions. Conveniently, in the distracted condition of the body portions, with the cam device located therebetween, the wires are displaced from the grooves in diametrically opposed directions.

Preferably the outer surface of both implants is a porous titanium material for permitting and encouraging bony ingrowth and complete anchorage of the implant within the bone of the vertebrae.

Figure 2:
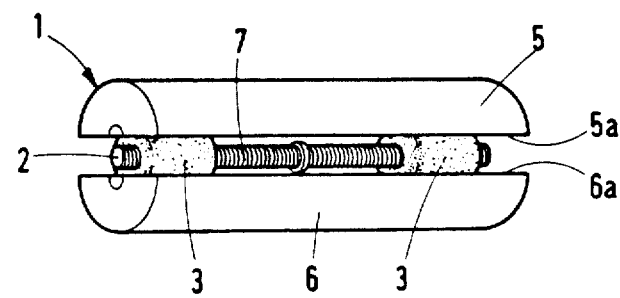
Figure 3:
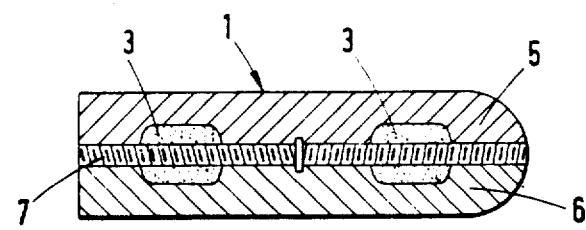
Figure 4:
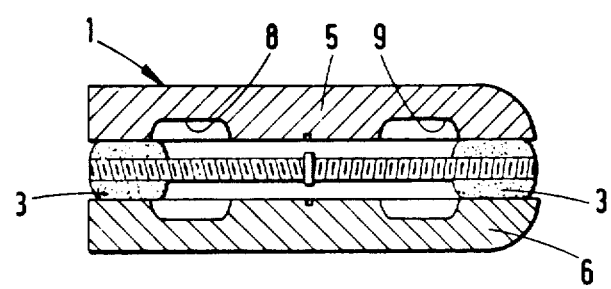
Figure 5:
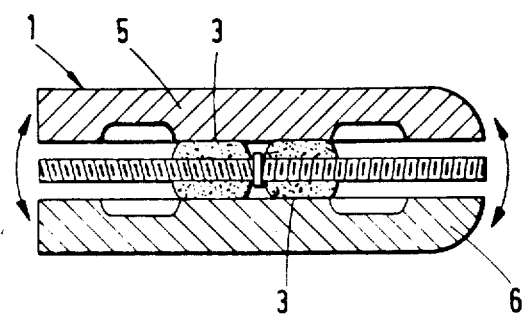
Figure 6:
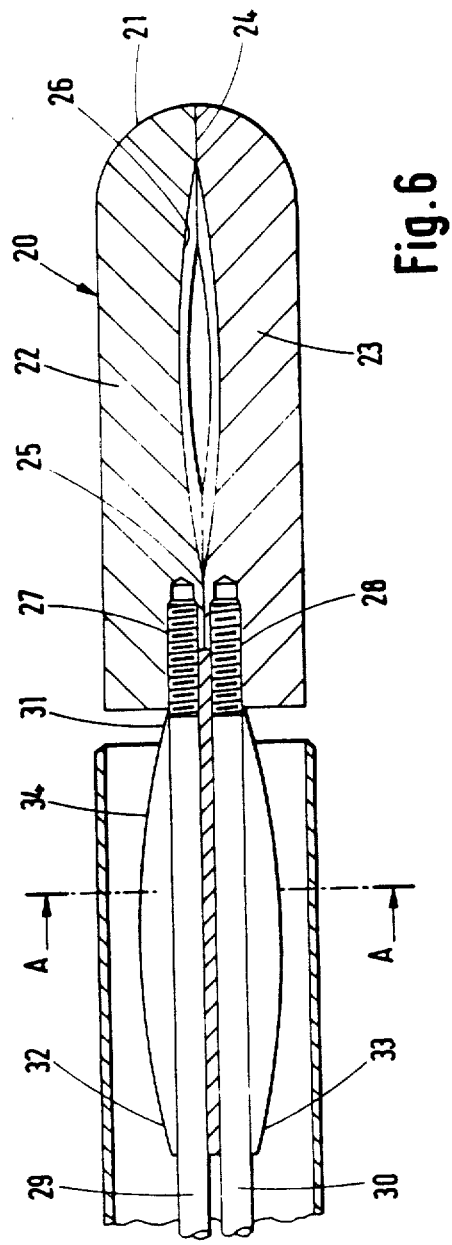
Figure 7:
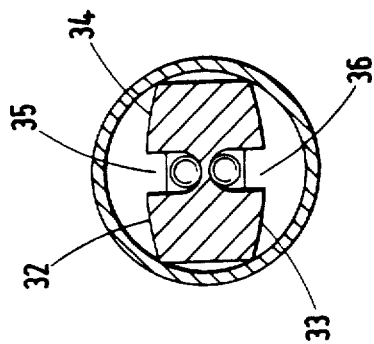

Embodiments of this invention will now be described by way of example with reference to the accompanying drawings in which:

FIG. 1 is an external perspective view of a first embodiment of a spinal implant according to the present invention, FIG. 2 is a perspective view of the implant of FIG. 1 with the portions of the body of the implant in a spaced apart condition, FIG. 3 is a cross-sectional view of the spinal implant in a closed 5 position, FIG. 4 is a cross-sectional view of the spinal implant of FIG. 3 in an expanded and locked position, FIG. 5 is a view similar to that shown in FIG. 4 but with the implant in an expanded rocking condition, FIG. 6 is a part sectional side elevational view of a second embodiment of a spinal implant according to the present invention and part of an insertion instrument, FIG. 7 is a cross-sectional view along the line A—A of FIG. 6, FIG. 8 is a view similar to that in FIG. 6 with the spinal implant in an expanded condition, and FIG. 9 is an end view from the left hand end of FIG. 8.

Referring in detail to FIGS. 1 through 5, one spinal implant comprises ane longate cylindrical body 1, an elongate rod 2 extending along the longitudinal axis of the body 1, and two cam devices 3 mounted on the rod 2.

In the closed position illustrated in FIG. 1 the elongate body 1 is cylindrical with a central elongate circular aperture 4 extending the whole length of the body for receiving the rod 2. The body itself is divided into two equal portions 5, 6 which simply abut each other along flat contact surfaces 5A and 6A, and including an elongate recess on each portion thereby defining the aperture 4 therebetween.

The elongate rod 2 has an external screw thread 7 along the whole of its length which mates with an internal screw thread of an elongate central aperture 20 through the cam devices 3. Screw thread 7 is divided into two oppositely pitched threads, one left-handed and the other right-handed so that upon rotation of the rod 2 in one direction the cam devices 3 move in opposite directions either away from each other or towards each other in dependence upon the direction of rotation of the rod 2.

The aperture 4 extending along the body has, at least over part of its length, an internal diameter which is substantially identical to the external diameter of the rod 2. Along the length of the aperture 4 there are provided two recesses of eonlarged diameter which are each of a general size to receive a respective cam device 3 when the body is in its closed position shown in FIG. 1. The end surfaces of the cam devices 3 are sufficiently curved so that when they abut the ends of the recess 8, 9, the sleeve is force to pass from the recess and gradually separates the body portions until the cam devices are fully located between the body portions 5 and 6 as shown in FIGS. 4 and n5. The rod 2 can be provided at its end with either an Allen key drive or a diametrical slot for receiving the head of a screw driver. The rod 2 may be adapted to be rotated by any other suitable means.

The cam devices 3 are preferably nylon sleeves having an internal screw thread with the same pitch as the respective threaded portion of the rod 7.

In use the spinal implant is located between two vertebrae to replace the intervertebral disc therebetween and for this purpose the outer surface of the implant is of porous titanium to obtain sufficient bone ingrowth and thereby provide a sound interference fit with the adjacent vertebrae. Should any disadvantage arise with titanium, other materials such as chrome cobalt, stainless steel or ceramics could be used.

With the spinal implant in position the threaded rod 2 is turned clockwise using an Allen key, for example, in a suitable recess in one end of the rod 2. As the rod rotates in a clockwise direction the cam devices 3 travel towards the opposite ends of the body and as they do so they create a wedge between the body portions and subsequently a graduated expansion of the device to the expanded position shown in Fig. 4. By turning the rod in an anti-clockwise direction the cam devices 3 travel towards the centre of the device creating a similar expansion of the implant to that shown in FIG. 4. However, the FIG. 4 condition has the effect of providing a firm immovable implant whilst in the condition shown in FIG. 5 the extreme opposite ends of the body are rockable on the cam devices so that the body portions 5, 6 at the respective ends thereof are movable towards or away from each other. In this latter condition the required spacing between vertebrae is maintained but spinal movements are also maintained and thereby the spinal implant acts as a replacement of the normal intervertebral disc.

FIGS. 6 to 9 show a second embodiment of a spinal implant according to the present invention together with part of the barrel of a "pistol" like instrument used to locate a cam device between split body portions of the spinal implant.

The spinal implant specifically shown in FIGS. 6 to 9 comprises an elongate cylindrical body 20 rounded at one end 21 and divided into two substantially identical portions 22, 23. The portions 22, 23 in the closed position of the spinal implant have abutting flat surface portions 24, 25 at the opposite ends of the implant and a centrally located shallow recess 26 defined between the two portions 22, 23.

At the left hand end of the spinal implant 20, as shown in Figures 6 and 8, there is provided in each portion 22, 23 an elongate threaded bore 27, 28 respectively which are arranged to receive support rods or wires 29, 30 screw-threadinglye ngaged with bores 27, 28. As shown in FIG. 8 the body portions 22, 23 of spinal implant 20 are curved adjacent flat portions 25 to facilitate spacing of the body portions 22, 23 when a cam device 31 is to be located therebetween.

The cam device 31 is of a one piece construction and a generally rectangular cross-section having a flat upper and lower surfaces 32, 33 at opposite ends of cam device and a central outwardly curved surface portion 34 for location within the curved recess portions of the body defining the recess 26. As more clearly seen in FIGS. 7 and 9, the cam device 31 has elongate grooves 35, 36 on opposite sides thereof extending the whole length of the cam device 31. The grooves 35, 36 receive the wires 29, 20 respectively, which wires act to guide the cam device 31 to engage the sloping surfaces at the left hand end of the spinal implant as shown in FIGS. 6 and 8. As the cam device is forced between the body portions 22, 23 of the spinal implant 20 the wires 29, 30 move in dimetrically opposite directions to allow the cam device to be located between the parts of the spinal implant. A left hand end view of the spinal implant in FIG. 8 is shown in FIG. 9 where the wires are shown to be completely disengaged from the grooves 35, 36.

The spinal implant shown in FIGS. 6 to 9 is of the fixed type where the cam device once located between the body parts of the spinal implantn fix the body portions 22, 23 relative to each other because of the contact between the flat surfaces 32, 33 and the flat surface portions 24, 25 of the body portions. However, to achieve a spinal implant in which the body portions can rock one relative to the other a cam device is provided which has outwardly curved portions 34 but does not have the flattened surface portions 32, 33 so that the curved portions 34 define a rocking surface for the curved recessed parts of the body portions defining the recess 26.

This second embodiment of the spinal implant according to the present invention also has an outer surface which is or porous titanium to obtain sufficient bone ingrowth and provide a sound interference fit with the adjacent vertebrae. Chrome cobalt, stainless steel or ceramics can also be used. Whilst the cam device is slidable in the longitudinal direction of the spinal implant 20 to achieve a slight amount of movement in the transverse direction between the two body portions the spacing between the two body portions is mainly controlled by preselecting the thicknesses of the cam device.

Preferably, the outside diameter of the wires 29, 30 are 1.7 mm (10 p.a.) and the maximum separation achieved by the wires, as shown in FIG. 9, is less than 10 mm.

The implant instrument has an elongate barrel part of which is shown in FIGS. 6 and 8. The barrel of the "pistol" instrument is of a circular configuration as shown in FIGS. 6 and 7 and has an internal diameter which is sufficiently large to support the cam device 31 which engages the internal surface of the barrel along each of four corners thereof whilst pressure is applied to the cam device to force it between the body portions 22, 23 of the spinal implant.

In use, the body portions 22, 23 are positioned in the intervertebral and the cam device is interposed between the body portions to push them apart. The concave surfaces of the recess 26 locate with the convex surfaces of the cam device. To enable rocking between the body portions and the cam device the convex surfaces of the cam device must be opposite one another. In some cases no rock is required and in this situation the cam device is provided with flat parallel surfaces at each end of the convex surfaces.

The body portions are initially suspended on wires outside the barrel of the implant instrument and are introduced into the joint space between adjacent vertebrae. The threaded support wires 29, 30 which are mounted on the pistol unit and extend from the barrel of the "pistol" are dis-engaged from the threaded bores of the body portions. The cam device which is initially located in the barrel of the pistol is pushed out of the barrel of the insertion device between the two halves of the spinal implant to separate them. Once the cam device is in position the wires are unscrewed from the body portions and the "pistol" instrument is withdrawn.

The grooves in the cam device allow the supporting wires attached to the body portions to be close together in a non distracted arrangement so that upon distraction the maximum separation is less than 10 mm. This is necessary to avoid a bolt in nerve damaging instrument.

The maximum spacing between the wires it not limited to 10 mm since in an alternative construction the external peripheral edge of the body portions rather than at the central location of Fib. 7. In this alternative construction, even through the body portions are in contact with one another, the cam device is arranged to pass between the wires. Therefore, the grooves 35, 36 FIG. 7 are omitted from the cam device. In this case the rear end of the cam device, relative to the direction of movement from the pistol device when implanting the spinal implant, is provided with a threaded control bore in which is engaged a wire for applying pressure to the cam device during insertion thereof between the body portions of the spinal implant.

There has been described a various embodiments of a spinl implant in which the basic invention remains the same, that is, that a split body is pushed apart by an interposed cam device to recreate joint space. However, in the latterly described embodiment the interposed cam device is pushed into place rather than moved along a screw threaded device.

Therefore, there has been described spinal implants which can be permanently inserted between vertebrae and can be used in place of bone grafting methods in establishing distraction into body fusion. The spinal implants function both in the surface of the implant being made of a porous titanium material which has the propety of permitting and encouraging bone ingrowth and thereby complete anchorage and also in that the implants are split longitudinally and cntain an expansion device within its body. By moving the expansion devices vertebral end plate are separated and root canal size re-established. Furthermore, the implants are firmly fixed by a strong interference fit which will achieve immediate rigidity of the appropriate segment of the spine. Preferably, the implant is three centimeters in length by one centimeter in diameter. However, the implant can be of any other suitable size and can have a rectangular cross-section.

The spinal implants described herein are of an elongate cylindrical structure so that insertion of the implant betwen spinal vertebrae requires a minimum incision in both skin and cartilage tissue. The cylindrical implant can be provided with external flat surfaces which are for example parallel to the contact surfaces of each body portion to assist in preventing migration of the implant. In one alternative construction the body portions may be of an elongate rectangular shape to provide added stability to the implant although a slightly increased length of incision will be necessary.

As described the spinal implants may be coated in a porous material to facilitate bone and cartilage tissue growth into the surface of the implant. Alternatively the implant may have a smooth non-porous finish which is coated with a bioactive material such as a hydroxyapatite, for example, tricalcium phosphate, which reacts chemically with bone and cartilage tissue to provide bone or tissue attachment to the implant.

Whilst the above embodiments have been described as being divided into two portions the implant bodies can be divided into four portions to allow for expansion of the overall diameter of the spinal implants rather than expansion in just one plane.

The external shape of the cam device may be of differentt shapes to those disclosed herein and as particularly shown in the drawings, to improve the amount of rocking movement within the implant and hence increase the flexibility between adjacent vertebrae.

One alternative cam device has identical opposed external surfaces each of which has a continuous arcuate curve in the direction of its longitudinal axis from the front to the rear thereof. In a transverse direction to the longitudinal axis the opposed surfaces are straight at the extreme front and rear edges whilst gradually increasing in curvature towards the longitudinally centre of the cam device where also there is a central region where the opposed curved surfaces of the cam device almost meet along the edges of the cam devices.

In the cam device described with reference to FIGS. 6, 7 the opposed surfaces are arcuate but relatively thick flat side surfaces are provided along the whole length of the cam device. The side surfaces of the cam devices may be arcuate to more closely accord with the internal diameter of the barrel of the implant instrument, thus providing more support for the cam devices within the barrel.

In another form the cam device has a shape substantially identical with that shown in FIGS. 6 and 8 but has an addition, an extension at both the front and rear ends thereof with the opposed surfaces thereof being flat so that when located between the body portions of the implant the central part of the cam device lies in the recess defined between the body portions whilst the flat front and rear extensions are engaged by the flat surfaces of the body portions in front of and behind the recessed area thereof. Each of the front and rear extensions are conveniently spaced from the central portion of the cam device by transversely extending grooves.

Alternatively, the expansion device in at least the first described embodiment is replaced by a rotatable cam located in a compartment within the body of the implant so thatupon rotation of the cam expansion between parts of the spinal implant is achieved.

The cam device 3 on the screw-threaded rod 2 can be made to extend a spike from the body as the body parts separate to ensure location of the device within the bone.

I claim:

1. A spinal implant for insertion in the joint space between adjacent vertebrae comprising:
    an elongated member divided longitudinally into two body portions which are movable between an open position, in which an external surface of each body portion is adapted to engage an adjacent vertebrae, and as closed position in which opposign adjacent flat contact surfaces on each said body portion abut each other, said body portions having a recess in eah of said flat contact surfaces so that said recesses define, in said closed position, an elongated aperture located centrally along the spinal implant; and
    an expansion means adapted to be disposed within said aperture so as to move said body portions between said open and closed positions and adjust the joint spacing between adjacent vertebrae, said expansion means having cam means that engage oppositely pitched thread patterns on end portions of a rod assembly so that the rotation of said rod assembly causes the cam means to move in unison along said rod assembly and between said contact surfaces so as cause said body surfaces to be moved.

2. A spinal implant as claimed in claims 1 wherein the exterior surface of the implant is of a porous material.

3. A spinal implant as claimed in claims 1 wherein the exterior surface of the implant is smooth and coated with a bioactive material to chemically bond the bone and cartilage tissue of the vertebrae to the implant.

* * * * *